United States Patent
Miwa et al.

Patent Number: 5,653,693
Date of Patent: Aug. 5, 1997

[54] MEDICATED SYRINGE PREPARATION

[75] Inventors: Akira Miwa; Masahiko Kikuchi, both of Tokyo; Masaru Abe, Takaishi; Sachio Yokote, Yokohama, all of Japan

[73] Assignee: Daiichi Pharmaceutical Co., Ltd., Tokyo, Japan

[21] Appl. No.: 50,136

[22] PCT Filed: Sep. 10, 1992

[86] PCT No.: PCT/JP92/01157
§ 371 Date: Sep. 24, 1993
§ 102(e) Date: Sep. 24, 1993

[87] PCT Pub. No.: WO93/04712
PCT Pub. Date: Mar. 18, 1993

[30] Foreign Application Priority Data

Sep. 10, 1991 [JP] Japan .................................. 3-230596

[51] Int. Cl.⁶ .................................................. A61M 5/00
[52] U.S. Cl. ........................ 604/187; 604/181; 604/218; 524/136; 524/140; 524/145; 524/117; 524/118; 128/654; 128/653.4
[58] Field of Search .................. 524/83, 117, 118, 524/119, 136, 140, 145; 128/654, 653.4; 604/181, 187, 218

[56] References Cited

U.S. PATENT DOCUMENTS

| | | | |
|---|---|---|---|
| 4,463,113 | 7/1984 | Nakahara et al. | 524/117 |
| 4,569,736 | 2/1986 | Kosegaki et al. | 523/105 |
| 5,450,847 | 9/1995 | Kampfe et al. | 128/653.4 |

FOREIGN PATENT DOCUMENTS

| | | |
|---|---|---|
| 0 446 358 | 9/1991 | European Pat. Off. . |
| 0446358 | 9/1991 | European Pat. Off. . |
| 56-62843 | 5/1981 | Japan . |
| 58-1736 | 1/1983 | Japan . |
| 61-53344 | 3/1986 | Japan . |
| 62-209151 | 9/1987 | Japan . |
| 1-178541 | 7/1989 | Japan . |

*Primary Examiner*—Paul R. Michl
*Assistant Examiner*—U. K. Rajguru
*Attorney, Agent, or Firm*—Oblon, Spivak, McClelland, Maier & Neustadt, P.C.

[57] ABSTRACT

This invention relates to a preparation comprising a transparent syringe body or container, which has been obtained by molding a resin comprising, as a base material, a propylene polymer, and as a nucleating agent, a phosphoric ester represented by the following general formula (1):

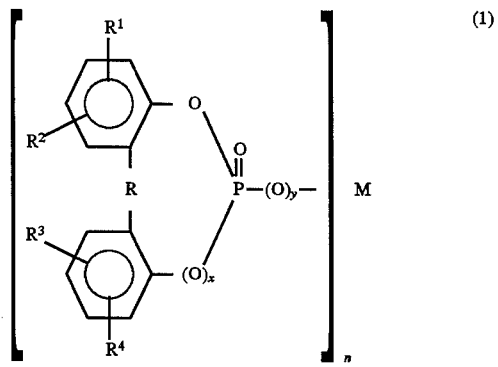

and a drug solution charged into the syringe body or container. The preparation is excellent in transparency, free from the dissolution of additives for the resin into the drug solution charged therein even when the drug solution remains charged for a long period of time and hence high in safety. The preparation is useful, in particular, as a syringe preparation charged with a drug solution therein.

8 Claims, No Drawings

MEDICATED SYRINGE PREPARATION

This application is a 371 of PCT/JP92/01157 Sep. 10, 1992.

TECHNICAL FIELD

The present invention relates to a preparation which comprises a transparent syringe body or container and a drug solution charged into the syringe or container (hereinafter may be referred to as "syringe preparation"), and is good in long-term stability, and to syringes and storage containers suitable for use in the production of such preparations.

BACKGROUND ART

Injections have heretofore been classified roughly into 2 types: a type in which a drug solution is charged into an ampule or vial to provide it, and then transferred from the ampule or vial to a syringe body on its use to inject it into a patient or the like, and another type in which a drug is charged into a vial in the form of powder or lyophilized amorphous powder, and then dissolved again so as to transfer it to a syringe body for its use and to inject it. These injections however have involved problems: i) prolonged time required for the transfer of drug solution, ii). complicated operation, iii) possibility of misoperation and iv) potential problem that glass powder may be mixed into the injections when ampules made of glass are used. In addition, since these injections must be transferred to syringe bodies for their use, they also pose v) a problem of bacterial contamination, the mixing of foreign matter, or the like when no longer sterile.

In order to solve these problems, small volumes of glass or plastic syringe bodies, in which a drug solution was charged in advance, have been investigated in recent years. In the plastic syringe bodies used conventionally, polypropylene resins with a sorbitol nucleating agent added thereto have been used in most of their resin materials. Therefore, they involve a problem that when a drug solution remains charged into such a syringe body for a long period of time, additives, decomposition products thereof and the like are dissolved out of the resin components.

In addition to the syringe bodies charged with a drug solution in advance, containers for infusions and containers for storing medicinal solutions such as a solution for injections, which are injected into the human body, for a long period of time involve a potential problem that since the drug solution comes into contact with a resin constituting such a container for a long time, additives for the resin may be dissolved out into the drug solution. Therefore, a thorough investigation has been required from the viewpoint of safety (the Japanese Pharmacopoeia, Testing Methods of Plastic Containers for Aqueous infusions, Dissolution Test, etc., Manual for the Japanese Pharmacopoeia, B-431). However, fully satisfactory results have not been yet obtained.

On the other hand, these syringe bodies and containers are required to have good transparency from the viewpoint of necessity of observing the turbidity of a drug solution charged therein by the naked eye and determining the amount of the drug which has been administered.

Accordingly, it is an object of this invention to provide a preparation comprising a syringe body or container and a drug solution charged into the syringe body or container, said syringe body or container maintaining its good transparency and being free from the dissolution of additives for a resin constituting the syringe body or container even when storing the drug solution for a long period of time, and moreover to provide a syringe body or container suitable for use in the production of such a preparation.

In view of the foregoing circumstances, the present inventors have carried out an extensive investigation. As a result, it has been found that when a drug solution is charged into a syringe body or container obtained by using a polypropylene resin containing, as a nucleating agent, a phosphoric ester represented by a general formula (1), which will be described subsequently, to mold it, a preparation which is free from the dissolution of additives for the resin and maintains the good transparency of the syringe body or container over a long period of time can be obtained, leading to completion of this invention.

DISCLOSURE OF THE INVENTION

Accordingly, the present invention is directed to a preparation comprising a transparent syringe body or container, which has been obtained by molding a resin comprising, as a base material, a propylene polymer, and as a nucleating agent, a phosphoric ester represented by the following general formula (1):

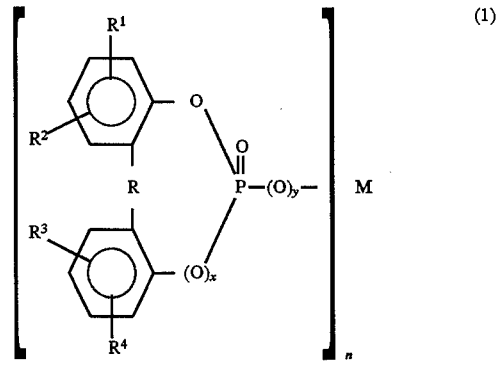

wherein $R^1$, $R^2$, $R^3$ and $R^4$ mean individually a hydrogen atom or a straight-chain, branched or cyclic alkyl which may be substituted, R denotes a direct bond, sulfur atom or alkylidene group, x and y stand individually for 0 or 1, M denotes a metal atom, and n means a valence of the metal, and a drug solution charged into the syringe body or container.

The present invention is also directed to a transparent syringe body or container suitable for use in the production of the above-described preparation.

BEST MODE FOR CARRYING OUT THE INVENTION

The preparation according to this invention is obtained by charging a drug solution into a syringe body or container in advance. The drug solution is desirably such that, it can be injected directly into the human body and is required to have high safety. As examples thereof, may be mentioned drug solutions for intravenous administration, intraarterial administration, intramuscular administration, subcutaneous administration and direct injection into organs, and the like. No particular limitation is imposed on the kind of the drug solution charged into the syringe body or container in advance. However, as examples thereof, may be mentioned drug solutions useful in the treatment or diagnosis of various diseases or disorders, Ringer's solution, various kinds of liquid nutritious agents, which are physiologically acceptable, and the like in the case where a large amount of a drug solution is administered, in particular, the syringe and syringe preparation according to this invention are useful. As examples of the diagnostic drug in the above-described drug solutions, may be mentioned various kinds of contrast media. The contrast media may include contrast media for radiography, MRI and ultrasonography. As examples of the contrast media for radiography, may be mentioned contrast media containing an iodine compound. The contrast media containing an iodine compound may include iohexol and iodixanol. As examples of the contrast media for MRI, may be mentioned (i) paramagnetic metal ions such as gadolinium (Gd), manganese (Mn) and dysprosium (Dy) and chelating agents thereof, (ii) ferromagnetic or ultraferromagnetic and ultraparamagnetic substances typified by various ferrites, (iii) nitrixide radicals, and (iv) ribosome preparations containing (i), (ii), or (iii). As examples of the contrast media for ultrasonography, may be mentioned contrast media comprising bubbles or capsules, in which minute bubbles such as bubbles of albumin are entrained or contained. As examples thereof, may be mentioned an albumin preparation ("Alubmex") designated so-called microbubbles, in which bubbles are entrained. In addition, contrast media for ultrasonography, which individually comprise various proteins, carbohydrates or pollers in place of albumin, may be mentioned. Further, the drug solution is not limited to aqeous solutions, and includes suspensions and oily solutions and suspensions. Further, examples of the preparation for include syringe bodies and storage containers for the drug solution. However, syringe bodies are preferred.

The composition of the resin used in the production of the syringe body or container according to this invention features that a propylene polymer as a base material and the above-described phosphoric ester (1) as a nucleating agent are contained. Here, the propylene polymer is not limited to a homopolymer of propylene, and includes crystalline copolymers with other monomers and blends of crystalline polypropylene and other polymers so long as they are polymers composed mainly of propylene. The crystalline copolymers composed mainly of propylene are preferably propylene-ethylene random copolymers and propylene-butene-1 copolymers. As examples of the other polymers blended with the crystalline polypropylene, may be mentioned ethylene-butene copolymers and the like. Of these propylene polymers, the propylene homopolymer and ethylene-propylene random copolymers obtained by copolymerizing propylene with 0.5-7 wt. % (preferably 0.5-5 wt. %) of ethylene are particularly preferred from the viewpoint of transparency. Further, of these propylene polymers, those having a melt flow index (MFI) of 0.5-100 g/10 min (more preferably 5-50 g/10 min) as measured in accordance with ASTM D-1238 are preferred.

The nucleating agent mixed with the resin used in this invention is a phosphoric ester represented by the above-described general formula (1). As examples of the alkylidene group indicated by R in the general formula (1), may be mentioned methylidene, ethylidene, isopropylidene, butylidene, hexylidene, octylidene, nonylidene, cyclopentylidene, cyclohexylidene and cyclooctylidene groups, etc.

As examples of the alkyl groups indicated by $R^1$, $R^2$, $R^3$ and $R^4$, may be mentioned methyl, ethyl, isopropyl, n-propyl, n-butyl, isobutyl, sec-butyl, tert-butyl, n-amyl, tert-amyl, hexyl, heptyl, n-octyl, 2-ethylhexyl, tert-octyl, nonyl, decyl, undecyl, dodecyl, tridecyl, tetradecyl, pentadecyl, hexadecyl, heptadecyl and octadecyl groups, etc. Further, as examples of the cycloalkyl group, may be mentioned cyclopentyl, cycloheptyl and cyclooctyl groups, etc.

As examples of the metal atom indicated by M, may be mentioned lithium, sodium, potassium, beryllium, magnesium, calcium, strontium, barium, zinc, aluminum, germanium, tin, lead, titanium, chromium, bismuth, molybdenum, manganese, iron, cobalt, nickel, zirconium, antimony, cadmium, etc. Of these, metals of Group Ia such as lithium, sodium and potassium and metals of Group IIa such as magnesium, calcium, strontium and barium are particularly preferred.

Typical compounds of the compounds used in this invention and represented by the general formula (1) are described in, for example, Japanese Patent Publication No. 8980/1988. These compound are shown below incidentally, the most typical compound of these compounds is sodium-2,2'-methylene-bis(4,6-di-tert-butylphenol)phosphate acid sodium phosphate (hereinafter abbreviated as "NA-11") represented by the following No. 1.

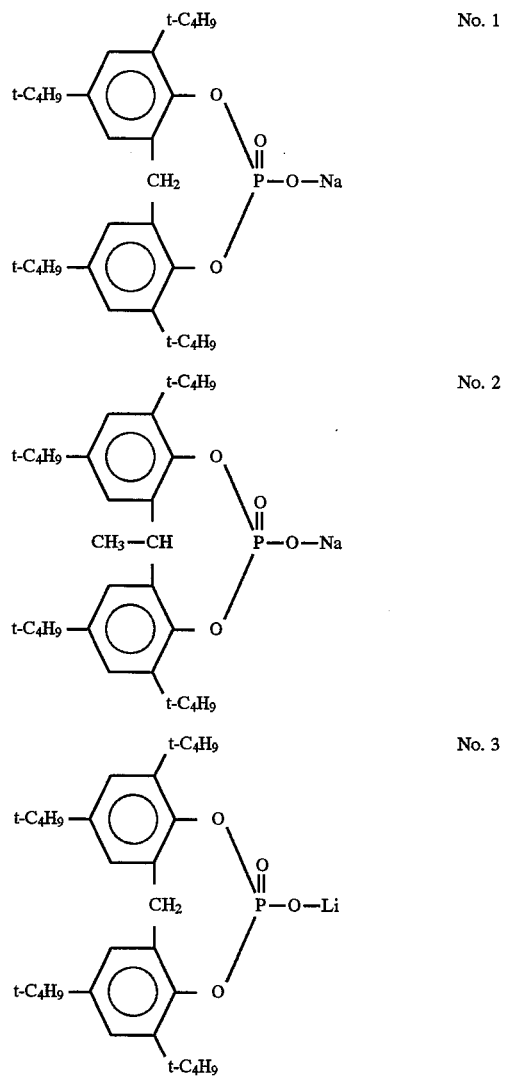

-continued
No. 4
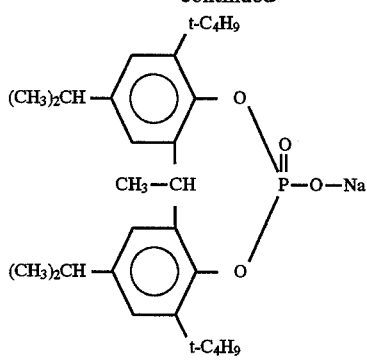
No. 5
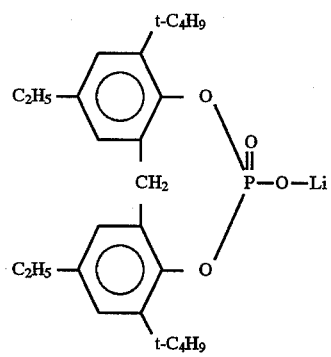
No. 6
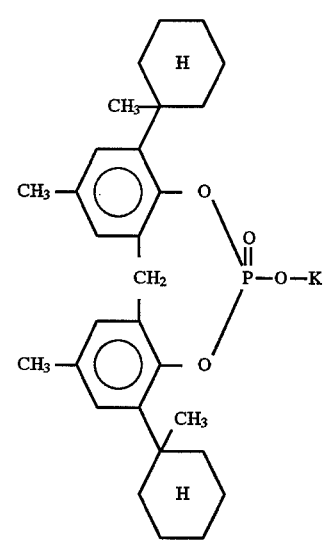
No. 7
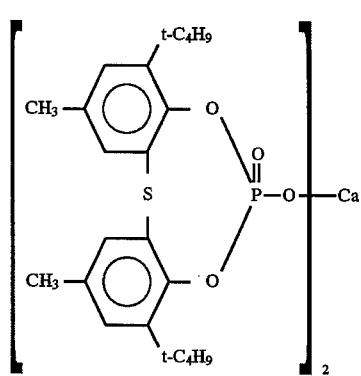
-continued
No. 8
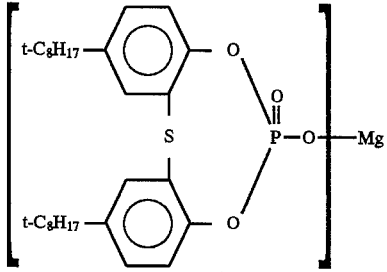
No. 9
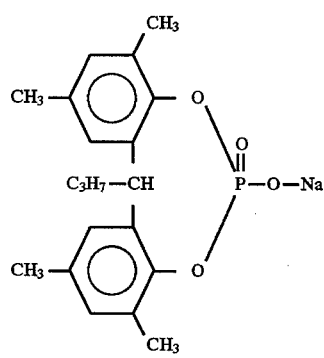
No. 10
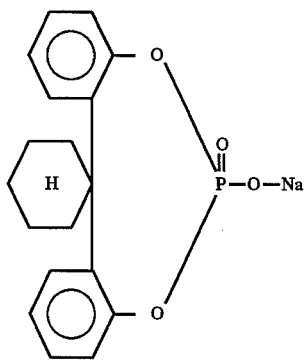
No. 11

-continued
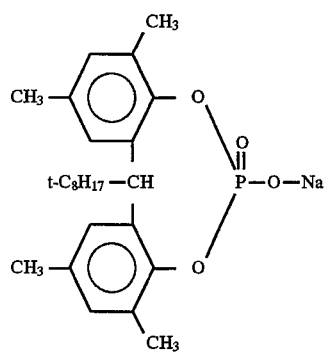
No. 12
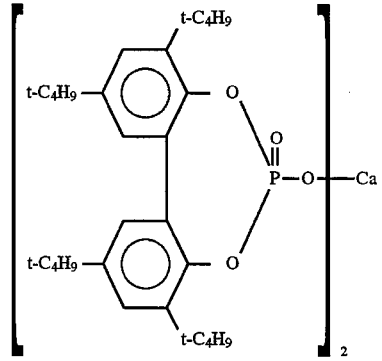
No. 16
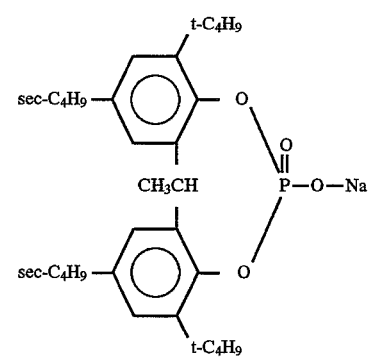
No. 17
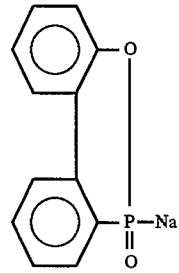
No. 13
No. 14
No. 15
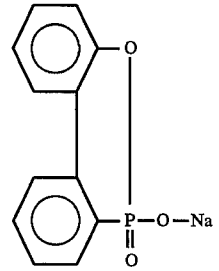
No. 18
No. 19
No. 20

No. 21
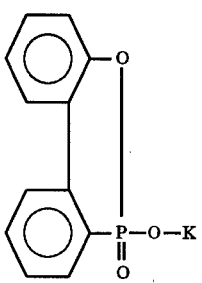

No. 22
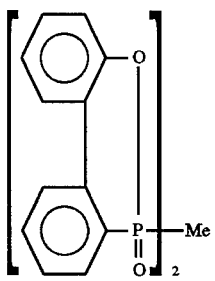

No. 23
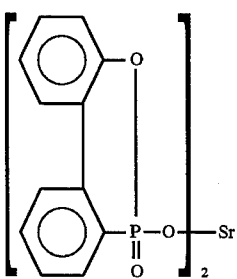

No. 24
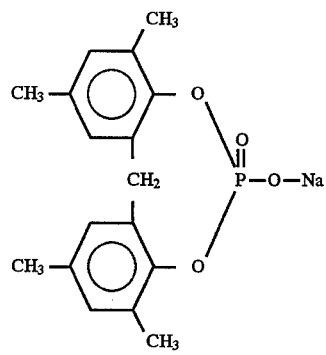

No. 25
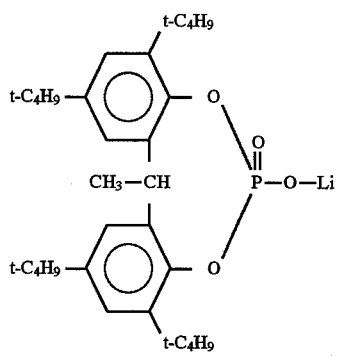

No. 26
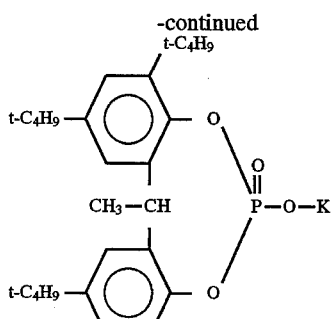

No. 27
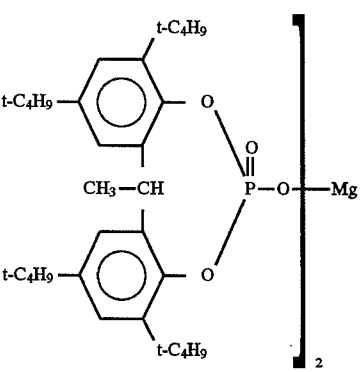

No. 28
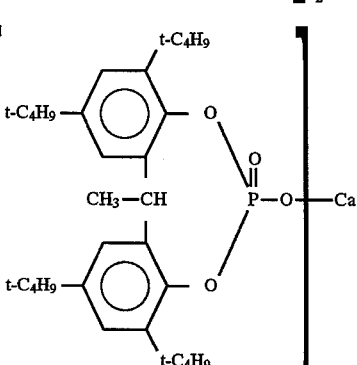

The amount of these phosphoric esters (1) to be added to the resin is preferably 0.001–5.0 wt. %, more preferably 0.01–3.0 wt. %, most preferably 0.05–0.5 wt. %. if the amount is less than 0.001 wt. %, the transparency of the resulting container or the like and the ability to prevent the dissolution where the drug solution is charged into the container become insufficient.

Further additives, for example, neutralizing agents, antioxidants, antistatic agents, organic peroxides, etc. may be suitably added to the resin useful in the practice of this invention.

As typical neutralizing agents which may be added to the resin according to this invention, may be mentioned metal salts of stearic acid, the oxides of alkaline earth metals, hydroxides of alkaline earth metals, basic salts and basic double salts.

The metal salts of stearic acid may include calcium stearate (hereinafter abbreviated as "STC"), magnesium stearate, zinc stearate and the like. Metal salts obtained by replacing stearic acid in the above-mentioned salts by other fatty acids may also be used. As exemplary preferred oxides and hydroxides of alkaline earth metals, may be mentioned magnesium oxide, calcium oxide and calcium hydroxide. As examples of the basic salts, may be mentioned those obtained by partially neutralizing the above-mentioned oxides and hydroxides with carbon dioxide, such as basic magnesium carbonate and basic calcium carbonate. As examples of the basic double salts, may be mentioned hydrotalcites which are hydrous basic carbonate minerals of magnesium and aiminum. These compounds may be used either singly or in combination. As particularly preferred alkaline earth metal compounds, may be mentioned magnesium oxide, magnesium hydroxide, basic magnesium carbonate, aluminum hydroxide and hydrotalcites.

As exemplary antioxidants, may be mentioned phenolic antioxidants, phosphite antioxidants, organic phosphite antioxidants, etc. As typical phenolic antioxidants, may be mentioned tetrakis [methylene-3(3',5'-di-tert-butyl-4'-hydroxyphenyl) propionate]methane ("Irganox 1010", trade mark, hereinafter abbreviated as "IRN"), 1,3,5-tris(3,5-di-tert-butyl-4-hydroxybenzyl) isocyanurate, 1,3,5-tris(3,5-di-tert-butyl-4-hydroxybenzyl)-2,4,6-trimethylbenzene and the like. In addition, those described in Japanese Patent Application Laid-Open No. 53344/1986 may be mentioned.

As a particularly preferred example of the organic phosphite compounds or organic phosphonite compounds, may be mentioned tris (2,4-di-tert-butylphenyl) phosphite ("Irgaphos 168", trade mark, hereinafter abbreviated as "IR168").

All the above-mentioned additives may be used in the resin material for the syringe body or container according to this invention. However, it is preferable to select them from the substances which have been permitted to use as additives by FDA in USA.

If an organic peroxide is added and a heat treatment is conducted, the melt flow index (MFI) of the resulting resin can be controlled. Such a treatment can improve the moldability and processability of the resin and hence the external appearance of a complicated molded product. As examples of the organic peroxide usable in the production of the resin material for the syringe body and container according to this invention, may be mentioned di-tert-butyl peroxide, tert-butyl peroxypivalate, lauroyl peroxide, benzoyl peroxide, cyclohexanone peroxide, tert-butyl peroxyisopropyl carbonate, tert-butyl peroxybenzoate, methyl-ethyl ketone peroxide, dicumyl peroxide, 2,5-dimethyl-2,5-di(tert-butylperoxy)hexane, 2,5-dimethyl-2,5-di(tert-butylperoxy) hexyne-3 and the like. These compounds may be used either singly or in combination.

In addition, the resin composition which is a material according to this invention may contain heavy metal deactivators, organotin compounds, plasticizers, epoxy compounds, pigments, fillers, foaming agents, fire retardants, processing aids, etc. as needed. Further, the resin composition according to this invention is desirably prepared without making use of any UV absorbent and lubricant. However, small amounts of the UV absorbent and lubricant may be contained so far as they do not impede the effects of this invention.

The proportion of the metal stearate to be added preferably falls within a range of 0.005–1.00 parts by weight per 100 parts by weight of the polypropylene resin. The proportion of the phenolic antioxidant to be added preferably falls within a range of 0.001–3.0 parts by weight, in particular, 0.005–1.0 part by weight per 100 parts by weight of the polyolefin. The proportion of the phosphite or phosphonite compound to be added preferably falls within a range of 0.001–5.0 parts by weight, in particular, 0.01–3.0 parts by weight per 100 parts by weight of the polyolefin. Preferably, the proportion of the organic peroxide to be added usually falls within a range of 0.001–0.5 part by weight per 100 parts by weight of the whole composition.

The syringe body or container according to this invention can be produced by molding a resin prepared in the following manner in accordance with a molding means such as injection molding. The production of the resin is performed, for example, by using, as a base material, the above-described propylene polymer, adding additives such as a nucleating agent, neutralizing agent and antioxidant to the polymer to mix them into an intimate dispersion, and then melting and pelletizing the dispersion by an extruder. Further, the molding is preferably carried out, for example, by melting under heat the thus-obtained pellets again and then molding the melt in an intended form in a temperature range of 180°–280° C., preferably, 230°±10° C. by the injection molding.

Using the resin container produced in the above-described manner, a process for making the drug solution into a preparation will hereinafter be described.

After the container produced by the above-described process, for example, a syringe body, is sterilized by autoclaving or sterilization with an ethylene oxide gas, a particular rubber stopper is put on the tip of the syringe body. Thereafter, a sterile drug solution (for example, a normal volume of a contrast medium) is charged by a filling machine under an aseptic operation environment- The amount of the solution charged may vary from 1 ml to 2000 ml, and is often within a range of from 50 ml to 150 ml. After the charging, the syringe body (a part where a plunger enters) is capped or vacuum capped with a plunger-cum-stopper for sealing, thereby producing a preparation.

Although the above-described example is a case where the drug solution is charged into the syringe body, drug solutions may also be charged into containers other than the syringe body to make them into preparations.

EXAMPLES

The present invention will hereinafter be described by the following Examples. However, it should be borne in mind that this invention is not limited to and by these Examples.

Example 1

(i)=Preparation Process of Synthetic Resin

With respect to Resin Nos. 1–7, a propylene-ethylene random copolymer containing 4 parts by weight of ethylene and having a melt flow index (MFI) of 20 (g/10 min) was used as a base material. Their corresponding components shown in Table 1 were used as additives. Namely, calcium stearate (STC) and/or "Hydrotalcite" (trade mark, HY) as neutralizing agents, and "irgafos 168" (trade mark, IR168), "Irganox 1010" (trade mark, IRN) and/or "Ultranox" (trade mark, UN) as antioxidants were added separately. "NA-11" (trade mark, NA11) was added as a nucleating agent in their corresponding proportions shown in Table 1. Further, 2,5-dimethyl-2,5-di(tert-butylperoxy)hexane (25Z) was added as an organic peroxide. These components were added to the base material in accordance with their corresponding formulations shown in Table 1 to mix them by a Henschel mixer into intimate dispersions.

Each of the resulting dispersions was melted and pelletized by a single screw extruder (barrel diameter:65 mm) at 230° C.

By these steps, resins containing the additives in varied proportions could be obtained. Resin No. 8 was prepared in the same manner as described above except that a propylene homopolymer having an MFI of 20 (g/10 min) was used as a base material.

The physical properties of these resins were tested. By this test, MFI (melt flow index, g/10 min) and haze (%) (according to ASTM D-1003) by making use of each molding sample of 2 mm thick were determined. The results are shown in Table 2.

In these physical properties, it was confirmed that the haze is well proportional to the transparency of the resin as determined by the naked eye in an aqueous solution or in the air.

These pellets were separately melted under heat again to mold them into intended syringe bodies at an injection temperature within a range of 230°±10° C.

TABLE 2

Physical properties of various plastic resins

| Test item | No. 1 | No. 2 | No. 3 | No. 4 | No. 5 | No. 6 | No. 7 | No. 8 |
|---|---|---|---|---|---|---|---|---|
| MFI* | 20 | 20 | 20 | 20 | 20 | 19.5 | 15 | 20 |
| Haze (%) | 85 | 80 | 41 | 35 | 34 | 38 | 25 | 49 |

*: MFI (melt flow index, g/10 min)

The syringe body or storage container for drug solutions according to this invention is required (a) to be free from the dissolution of the additives into its contents, i.e., water, a drug solution or other medicinal liquid and (b) to surely keep the transparency of the resin good for the purpose of

TABLE 1

Polypropylene synthetic resins containing various additives in combination

| | Additive | No. 1 | No. 2 | No. 3 | No. 4 | No. 5 | No. 6 | No. 7 | No. 8 |
|---|---|---|---|---|---|---|---|---|---|
| Neutralizing agent | STC | 0.04 | 0.08 | 0.08 | 0.08 | 0.08 | 0.08 | 0.07 | 0.08 |
| | HY | 0.03 | | | | | | | |
| Antioxidant | IR168 | | 0.045 | 0.045 | 0.045 | 0.045 | 0.045 | 0.1 | 0.045 |
| | IRN | 0.05 | 0.045 | 0.045 | 0.045 | 0.045 | 0.045 | | 0.045 |
| | UN | 0.05 | | | | | | | |
| Nucleating agent | NC4 | | | | | | | 0.30 | |
| | NA-11 | | | 0.10 | 0.20 | 0.30 | 0.20 | 0.20 | |
| organic acid[a] | 25Z | | | | | | 0.013 | | |
| UV absorbent | SN | | | | | | | 0.04 | |

Note:

Organic acid a): Organic peroxide.

b): Propylene homopolymer.

25Z: 2,5-Dimethyl-2,5-di(tert-butylperoxy)hexane.

STC: Calcium stearate (FDA No. 178. 2010).

IR168: Tris(2,4-di-tert-butylphenyl)phosphite ("Irgaphos 168", FDA No. 178. 2010)

IRN: Tetrakis-[methylene-3-(3',5'-di-tert-butyl-4-hydroxyphenyl) propionate]methane ("Irganox 1010", FDA No. 178. 2010)

NC4: 1,3,2,4-Di-(p-ethylbenzylidene)-sorbitol (FDA No. 178. 3295)

NA-11: Sodium-2,2'-methylene-bis(4,6-di-tert-butylphenyl)phosphate ("NA-11UY", FDA No. 178. 3295)

HY: Mixture of aluminum hydroxide and magnesium hydroxide ("Hydrotalcite", FDA No. 184. 1428)

UN: Di(2,4-di-tert-butylphenyl)pehtaerythritol diphosphite ("Ultranox 626", FDA No. 178. 2010)

SN: Dimethyl succinate-1-(2-hydroxyethyl)-4-hydroxy-2,2,6,6-tetramethylpiperidine polycondensate ("Sanol LS-622", FDA No. 178. 2010)

conducting the check test on foreign matter. Plastic containers have advantages of being light in weight, hard to break and easy to package and ship them. On the other hand, they are adversely affected by heat and light as time goes on, and their transparency is hence deteriorated. The opacity due to failure in transparency makes it difficult to check the foreign matter. They also involve a potential problem of dissolution of additives such as antioxidant, ultraviolet absorbent and plasticizer (stabilizer). By this fact, it is forecast that when the intended content is an injection, various toxicity such as toxicity to blood and acute toxicity due to these additives in the living body poses a serious problem because the injection is directly introduced into the human body (Japanese Pharmacopoeia B-439).

The plastic syringe bodies (containers) charged with a drug solution have not yet been satisfactorily put to practical use. Therefore, the criteria for their production are not established at present by the authorities concerned. However, the criterion of "Testing Methods of Plastic Container for Aqueous Infusions" (Japanese Pharmacopoeia) furnishes with some information. Accordingly, (1) the inspection of transparency and visual appearance and (2) a dissolution test are conducted in accordance with the Testing Methods of Plastic Container for Aqueous Infusions. In addition, (3) a drug stability test in a long term is required by chemical or physical detection of drug properties or qualities affected by storage in the syringe body or containers.

Their investigations will hereinafter be described by the following Examples. However, drug solutions according to this invention are not limited to the cases mentioned in these Examples.

Example 2

Dissolution Test (1)

Various polypropylene resins shown in Table 3 were used as samples to conduct tests in accordance with Dissolution Test in Testing Methods of Plastic Container for Aqueous Infusions prescribed by the Japanese Pharmacopoeia.

Portions of a container to be tested, which had the least possible curvature and were even in thickness, were taken as a sample to cut them. The cut pieces are collected in such a manner that when the thickness is not greater than 0.5 mm, the total surface area of both sides is about 1200 $cm^2$, and when the thickness exceeds 0.5 mm, the total surface area is about 600 $cm^2$. The thus-collected cut pieces were cut further in a size of 5 cm long and 0.5 mm wide, washed with water and then dried at room temperature. This sample was placed in a hard glass container having an internal volume of about 300 ml. After 200 ml of water was accurately added to the container and the container was hermetically sealed with a suitable stopper, the sample was heated for 1 hour at 121° C. by an autoclave and left to stand until it was cooled to room temperature. The thus-obtained liquid was taken as a test liquid.

On the other hand, a blank test liquid was prepared in the same manner as described above except that water alone was used. With respect to the test liquid and blank test liquid, the following tests were performed.

i) Detection test of ammonium ion and the like:

Ten milliliters of the test liquid were put into a Nessler tube and water was added to 50 ml. To the resulting liquid mixture, were added 2.0 ml of an aqueous solution prepared by adding water to 1 g of sodium hydroxide to 3 ml and 1.0 ml of a Nessler test solution. The Nessler tube was thoroughly shaken. The color of the test liquid was compared with the color in the case where the following comparison solution was used. As the comparison solution, was used a solution prepared by adding water to 0.5 ml of an ammonia standard solution substituting for the test liquid to 10 ml. The comparison solution was operated in the same manner as described above.

The ammonia standard solution is prepared in the following manner. Namely, 2.97 g of ammonium chloride is accurately weighed and dissolved in purified water for ammonium test to prepare precisely 1000 ml of an aqueous solution. Ten milliliters of this solution are precisely measured out and added with purified water for ammonium test to 1000 ml. This solution contains ammonium ion ($NH_4^+$) in a proportion of 0.01 mg per This test is based on a reaction in which ammonium ions are detected by a Nessler test solution. However, amines, glucose and the like become positive. The acceptance limit is 0.05 μg/ml in terms of ammonium ion ($NH_4^+$). As apparent from the test results shown in Table 3, Resin No. 7, which contained a sorbitol nucleating agent, did not pass the standard of the criterion (the ammonium test in the dissolution test of Testing Methods of Plastic Container for Aqueous Infusions prescribed by the Japanese PharmaCopoeia). However, Resin Nos. 1–6 and No. 8 which contain no nucleating agents or contain a phosphoric nucleating agent passed the standard.

ii) Detection test of substances reducing potassium permanganate:

Twenty milliliters of the test liquid was placed in a stoppered conical flask, to which 20 ml of a 0.01N solution of potassium permanganate and 1 ml of dilute hydrochloric acid were added. After the contents were boiled for 3 minutes and then cooled, 0.10 g of a potassium iodide solution was added thereto. After the flask was sealed with a stopper, shaken and then left over for 10 minutes, the contents were titrated with a 0.01N sodium thiosulfate solution (indicator: starch solution, 5 droplets).

On the other hand, using 20.0 ml of a blank test liquid as a control, the same procedure was followed. The samples were regarded as passing the test when the difference in the 0.01N potassium permanganate consumed was 1.0 ml. or lower, and not passing the test when exceeded 1.0 ml.

As apparent from Table 3, Resin No. 7, which contained a sorbitol nucleating agent, did not pass the test. On the other hand, the consumptions of Resin Nos. 1–6 and No. 8 were 1.0 ml or less, and they hence met the standard.

iii) Detection test of substances absorbing ultraviolet rays:

The acceptance standard where a test was conducted on each test liquid in accordance with the absorbance measuring method using the blank test solution as a contrast is 0.08 or lower in terms of absorbancy at a wavelength of 220 nm (inclusive) to 241 nm (exclusive), or 0.05 or lower in terms of absorbancy at a wavelength of 241 nm to 350, both inclusive.

As apparent from Table 3, Resins No. 1–6 and No. 8 met the detection test of substances absorbing ultraviolet rays.

TABLE 3

Dissolution test for various plastic resins

| | Test item | | | |
|---|---|---|---|---|
| | | Substance reducing potassium per- | UV absorption spectrum | |
| Resin | Ammonium, etc. Compared with | manganate | | |
| No. Ref. value | comparison liquid Not deep | Difference from blank ≦1.0 ml | 220– 240 nm ≦0.08 | 241– 350 nm ≦0.05 | Judgment |
| No. 1 | Not deep | −0.40 | 0.017 | 0.015 | Met |
| No. 2 | Not deep | +0.03 | 0.027 | 0.013 | Met |
| No. 3 | Not deep | −0.02 | 0.038 | 0.005 | Met |
| No. 4 | Not deep | −0.17 | 0.048 | 0.007 | Met |
| No. 5 | Not deep | −0.33 | 0.045 | 0.008 | Met |
| No. 6 | Not deep | −0.20 | 0.027 | 0.004 | Met |
| No. 7 | Deep | −1.50 | 0.260 | 0.082 | Not met |
| No. 8 | Not deep | −3.0 | 0.070 | 0.009 | Met |

Example 3

Dissolution Test (2)

Resin No. 4 (thickness: about 0.5 mm, surface area: 1200 $cm^2$) prepared in Example 1 was ground and added with 400 ml of distilled water, followed by treatment by an autoclave for 1 hour at 121° C. The thus-obtained extract was evaporated to dryness at about 60° C. under nitrogen, thereby obtaining 4.3 mg of a dry solid sample. With respect to the thus-obtained dry solid sample, infrared absorption spectrum analysis (IR), high performance liquid chromatography (HPLC) and gas chromatography (GC) were performed to inspect whether the additives were dissolved out of the resin or not. Incidentally, measuring conditions for HPLC and GC are as follows:

HPLC: wavelength 284 nm (UV), column Shodex GPC K-802×2

GC: Detector FID, Shilicon OV-12%, Chromosorb W (AW-DMCS), mesh 80–100, 2 m×3 mm across, glass As a result, absorption was observed at 3300–3500 cm$^{-1}$, about 1600 cm$^{-1}$, 1230 cm$^{-1}$ and 1000 cm$^{-1}$ in IR. These absorption was deduced to be the absorption attributed to the base material of the resin. No absorption attributed to the additives was observed. In HPLC, no peak corresponding to the additives was observed in both UV detection and IR detection. Further, no particular peak was observed in GC. Since the limit of detection for the additives, IR168 and IRN, by HPLC (UV) is 0.1 ppm or less, it was confirmed that these additives were dissolved out of the resin only by at most 0.1 ppm.

Example 4

Transparency Test for Plastic Resin

Polypropylene resins for the various plastic resins shown in Table 4 were separately molded into plates having a thickness of 2 mm to use them as samples. Their transparency was evaluated by the naked eye.

It has been known that polypropylene is essentially an opaque material, but its transparency can be improved by adding a nucleating agent and/or the like thereto. Accordingly, the plate of No. 7, which was most superior in transparency, was supposed to be 100 to score the transparency of the various plates. In the score, a greater numerical value indicates higher transparency. The evaluation of the transparency was conducted in both air and distilled water.

TABLE 4

Transparency of resins

| Resin No. | In air | In distilled water |
|---|---|---|
| No. 1 | 14 | 14 |
| No. 2 | 29 | 29 |
| No. 3 | 45 | 57 |
| No. 4 | 71 | 78 |
| No. 5 | 83 | 71 |
| No. 6 | 100 | 100 |
| No. 8 | 38 | 42 |

It is understood from the above-described results that when a nucleating agent, NA-11 ("NA-11UY") was added to Resin No. 2 to prepare resin materials such as Resin Nos. 3, 4 and 5, the transparency was significantly improved as demonstrated by scores of at least 45 (in air) and at least 57 (in distilled water).

Therefore, it was definitely shown that the use of Resin Nos. 3–5, to say nothing of Resin No. 6, as containers for drugs does not interfere with the detection of contents by the naked eye or the like.

Example 5

Study of Interaction between Drug and Resin (1)— Effect on drug stability—

Taking "Omnipaque" (trade name) as an example of a drug, an investigation of interaction between the drug and a resin was first of all conducted. Omnipaque is a contrast medium comprising, as an active ingredient, iohexol[(±)-N, N'-bis(2,3-dihydroxypropyl)-5-[N-(2,3-dihydroxypropyl)-acetamide]-2,4,6-triiodoisophthalamide]. Omnipaque 240 is a preparation containing 240 mgI/ml of iohexol as an active ingredient.

A polypropylene resin sheet (thickness:0.5 mm) having a composition corresponding to Resin No. 4 was cut into pieces of 5×0.5 cm. The liquid contrast medium was added in a proportion of 200 ml per 600 cm$^2$ of the surface area. The resulting mixture was autoclaved for 1 hour at 121° C. The thus-obtained solution was used as a sample to conduct such an investigation as described below.

The external appearance of the solution was observed by the naked eye and its pH was measured in accordance with pH Determination of General Tests prescribed by the Japanese Pharmacopoeia.

The osmotic pressure ratio was determined in accordance with Osmotic Pressure Determination of General Tests prescribed by the Japanese Pharmacopoeia.

The UV absorption was determined as to a solution, which had been prepared by adding water to 1 ml of the sample to 500 ml and then further adding water to 1 ml of this liquid mixture to 100 ml, in accordance with Absorbance Determination of General Tests prescribed by the Japanese Pharmacopoeia. The determination of iodine and iodides was conducted in the following manner. The sample in a volume corresponding to 1.0 g of the contrast medium was taken out and 4 ml of water was added to this sample portion to mix them, followed by addition of 1 ml of dilute hydrochloric acid. The resulting mixture was left over for 10 minutes while sometimes shaking up the mixture. Further, 5 ml of chloroform was added and the resulting mixture was thoroughly shaken up and left to stand. The chloroform layer was colorless.

Next, 1 ml of a sodium nitrite solution (0.02 g/ml) was added to the above mixture and then shaken up. After the resultant mixture was left to stand, the chloroform layer was separated. Using, as a control, a chloroform layer obtained by processing in the same manner as described above except for the use of 4 ml of water, the absorbance of the dispersion was determined at a wavelength of 510 nm in accordance with Absorbance Determination of General Tests prescribed by the Japanese Pharmacopoeia. As a result, it was found to be not higher than the absorbance of a comparison solution (Table 5).

TABLE 5

Interaction between iodo contrast medium[a] and Resin No. 4

| | Sample | |
|---|---|---|
| Test item | Blank | Resin No. 4 |
| Appearance | Colorless transparent solution | Colorless transparent solution |
| pH | 7.24 | 7.25 |
| Osmotic pressure ratio | 2.2 | 2.2 |
| UV absorption | $\lambda_{max}$: 245–246 nm | $\lambda_{max}$: 245–246 nm |
| Iodine and iodide | Iodine: not detected Iodide: 27.4 ppm | Iodine: not detected Iodide: 27.4 ppm |
| Content (%) | 100.0 | 100.0 |

[a] The iodo contrast medium was a contrast medium comprising, as an active ingredient, iohexol.

The comparison solution was prepared in the following manner. Namely, 0.131 g of potassium iodide was accurately weighed and water was added to precisely make a 1000 ml solution, thereby dissolving it. This solution was precisely measured out by 2 ml and added with 3 ml of water and 1 ml of dilute sulfuric acid. The subsequent process was the same as described above.

It was shown from the above results that Resin No. 4 has no effect on the stability of the contrast medium.

Example 6

Interaction between Drug and Resin (2)—Effect on drug stability—

In this test, "Transamin S Injection" (trade name) was used as a drug solution. Transamin S Injection is an injection containing tranexamic acid [trans-4-aminomethyl-cyclohexanecarboxylic acid] (1 g/10 ml, 250 mg/2.5 ml). The polypropylene resin sheet (thickness:0.5 mm) for plastic syringes was cut into pieces of 5×0.5 cm. Transamin S Injection was added in a proportion of 200 ml per 600 $cm^2$ of the surface area. The resulting mixture was autoclaved for 1 hour at 121° C. The thus-obtained solution was used as a sample to conduct such an investigation as described below (Table 6). The external appearance of the solution was observed by the naked eye and its pH was measured in accordance with pH Determination of General Tests prescribed by the japanese Pharmacopoeia. The osmotic pressure ratio was determined in accordance with Osmotic Pressure Determination of General Tests prescribed by the Japanese Pharmacopoeia. The content of tranexamic acid was determined by such formol titration as described below. Namely, 10 mg of this sample was precisely weighed and added with 50 ml of water and 3 ml of neutralized formalin.

The thus-obtained mixture was subjected to potentiometric titration with a 1N sodium hydroxide solution. A blank test was conducted in the same manner to correct the titration value. In this titration, 1 ml of the 1N sodium hydroxide solution corresponds to 157.21 mg of $C_8H_{15}NO_3$. The neutralized formalin used was prepared by adding a 0.1N sodium hydroxide solution to formalin (37%) to adjust its pH to 7.5.

As a result, no difference from the blank was observed in all the test items of the appearance, pH, osmotic pressure ratio and drug content. Accordingly, it was suggested that Resin No. 4 has no effect on the quality of the tranexamic acid preparation.

TABLE 6

Interaction between tranexamic acid and Resin No. 4

| | Sample | |
|---|---|---|
| Test item | Blank | Resin No. 4 |
| Appearance | Colorless transparent solution | Colorless transparent solution |
| pH | 7.61 | 7.60 |
| Osmotic pressure ratio | 2.3 | 2.3 |
| Content (%) | 100.7 | 100.0 |

Example 7

Interaction between Drug and Resin (2)— Durability—

Effects of a contrast medium solution containing 300 mgI/ml of iohexol on the physico-chemical properties of a polypropylene resin were investigated.

A polypropylene resin sheet (thickness:0.5 mm) having a composition corresponding to Resin No. 4 was cut into pieces of 5×0.5 cm (surface area:600 $cm^2$). The thus-obtained sample was immersed in 200 ml of distilled water or the contrast medium solution and stored for 1 month at 60° C. Thereafter, the sample was tested on the physico-chemical properties shown in Table 7. Incidentally, the results of a test which was conducted after storing the resin for 1 month in the air of 60° C. are also shown collectively in Table 7.

TABLE 7

| | | | Liquid to be immersed | | |
|---|---|---|---|---|---|
| Test item | Testing method | At start | Air | Distilled water | Contrast medium solution |
| Yield strength | ASTM D-1238($kg/cm^2$) | 339 | 353 | 349 | 348 |
| Elongation | ASTM D-638(%) | 709 | 486 | 489 | 570 |
| Flexural strength | ASTM D-790($kg/cm^2$) | 421 | 472 | 468 | 453 |
| Flexural modulus | ASTM D-790($kg/cm^2$) | 13700 | 15600 | 15700 | 15400 |
| Dupon't 23° C. impact −10° C. value | According to JIS K-6718 (kg · cm/1/2" Φ) | 43–43 <1.5 | 38–39 <1.5 | 38–40 <1.5 | 36–39 <1.5 |
| Izod. 23° C. impact −10° C. value | ASTM D-256 (kg · cm/cm) | 3.6 1.8 | 3.7 1.8 | 4.0 1.8 | 3.7 1.8 |
| Rockwell hardness | ASTM D-785(R) | 102 | 106 | 106 | 106 |
| Heat distortion temperature | ASTM D-523(°C.) | 105 | 110 | 107 | 109 |
| Gloss | ASTM D-523(%) | 100 | 98 | 97 | 99 |
| Haze | (%) | 38 | 43 | 42 | 43 |

As a result, it was decidedly confirmed that Resin No. 4 undergo no changes of its physico-chemical properties even after it has been brought into contact with water or the drug solution for a long period of time, and is hence excellent in durability.

Example 8

Durability of Syringe Body

The preparations according to this invention are intended to distribute syringe bodies or containers with a drug solution charged therein. If they are broken in the course of the distribution, the drug solution flows out. Therefore, such syringe bodies and containers are required to have sufficient durability. Thus, a durability test was conducted on syringe bodies (molded products) under severe conditions.

(1) Evaluation items:

Bending test, compressive test, pressure test, drop test and exposure test to light (all the tests were conducted with reference to the testing methods for plastics prescribed by JIS).

(2) Severe conditions:

Exposure conditions as to temperature and light were preset to 70° C. for 10 days and 5° C. for 3 months, and 1,800,000 Lx.h, respectively. These severe tests are conducted on both autoclaved syringe bodies and unautoclaved syringe bodies.

(3) Preparation of samples:

Exposure to both temperature and light was conducted in a state that the contrast medium solution containing 300 mgI/ml of iohexol was charged in an amount of 102 ml. With respect to the syringe bodies subjected to the exposure to temperature, the tests were conducted after they were conditioned for at least 40 hours at 25° C. and 50% RH after the exposure.

(4) Test results:

As a result, it was demonstrated that syringe bodies made of Resin No. 4 undergo no changes in the bending, compressive, pressure, drop and light exposure tests even under the conditions of temperature and exposure to light, which are considered to be considerably severe compared with the conditions in the ordinary course of their distribution, and are hence excellent in durability (Table 7).

Example 9

Long-Term Stability of Preparation Containing Contrast Medium

A syringe preparation which comprised a contrast medium solution containing 240 mgI/ml of iohexol in an amount of 100 ml was produced and stored for 6 months under conditions of 40° C. and 75% RH. Testings for property, identification, pH, purity, insoluble foreign matters and pyrogens, aseptic test and measurement of content were conducted at the time of beginning of storage and upon elapsed time of 1 month, 2 months, 3 months and 6 months after the beginning of storage in accordance with the testing methods described in the revised eleventh Japanese Pharmacopoeia.

As a result, as shown in Table 8, the preparation according to this invention showed no abnormal signs even when stored for 6 months under the severe conditions, and was hence stable.

TABLE 8

| Test item | At start | 1 month | 2 months | 3 months | 6 months |
|---|---|---|---|---|---|
| Property: | | | | | |
| Appearance | Colorless transp. soln. | Colorless transp. soln. | Colorless transp. soln. | Colorless transp. soln. | Colorless transp. soln. |
| Osmotic ratio[1] | 1.84–1.89 | 1.78–1.92 | 1.73–1.87 | 1.84–1.88 | 1.77–1.87 |
| Identification: | | | | | |
| (1) Iodine | Purple vapor generated | Purple vapor generated | Purple vapor generated | Purple vapor generated | Purple vapor generated |
| (2) UV absorption spectrum (nm) | 245.0–246.0 | 245.0–246.0 | 245.0–246.0 | 245.0–246.0 | 245.0–246.0 |
| pH[1] | 7.34–7.42 | 7.23–7.38 | 7.21–7.43 | 7.15–7.32 | 7.18–7.30 |
| Purity test: | | | | | |
| (1) Aromatic primary amine[1] | 0.181–0.189 | 0.175–0.190 | 0.175–0.183 | 0.173–0.181 | 0.172–0.198 |
| Iodine | Colorless | Colorless | Colorless | Colorless | Colorless |
| (2) Iodine and iodide | | | | | |
| Iodide[1] (ppm) | 0.0–7.0 | 5.4–19.5 | 7.1–16.9 | 8.3–13.5 | 11.9–19.1 |
| Aseptic test | Aseptic | — | — | — | Aseptic |
| Insoluble foreign matter | Met | Met | Met | Met | Met |
| Pyrogen test | Negative | — | — | — | Negative |
| Content[1] (% vs. nominal amount) | 99.0–101.4 | 99.0–101.4 | 99.2–100.9 | 98.5–101.4 | 99.1–101.5 |

Remarks Note [1]: Test was repeatedly conducted three times, and the measurement value was indicated by the width of the minimum value and the maximum value in three tests.

Example 10

Clinical Test

Using a syringe preparation (made of Resin No. 4) of this invention, in which a contrast medium had been charged as a drug solution, a clinical test was conducted to evaluate the effectiveness, stability and usability of the preparations.

(Method)

Syringe preparations charged with contrast media containing iohexol in proportions of 240 mgI/ml (100 ml) or 300 mgI/ml (50, 100 ml) were separately attached to an automatic injector. The drug solutions were separately administered in a dose of from 40 ml to 100 ml at high or low speed or in combination thereof through a vein of the back of a hand, the instep of a foot or an elbow by the automatic injector (manufactured by Nemoto Kyorindo K. K.)

(Results)

(1) Effectiveness:

In substantially all cases out of 258 cases in 16 institutions except for several cases where the judgment of effectiveness was difficult due to the trouble of machinery and the like, images which was high in contrast and of great diagnostic value could be obtained. Therefore, the preparations of this invention were identical in imaging effect to the conventional vial preparations.

(2) Stability:

With respect to side effects, nausea, vomiting, sneezing, flare, itching and/or the like developed in 7 cases out of 256. Further, slight heat sensation and pain were observed only in 1–2% of the total application cases. Side effects and toxicity which were considered to be caused by the fact that the drug was stored in the syringe (for example, granting that the resin components or additives for the resin in the syringe were dissolved out, side effects and toxicity caused by the dissolved matter) were not recognized at all.

Accordingly, the preparations according to this invention offered no problem in 97% of the application cases, and were hence judged to be identical to the conventional vial preparations.

(3) Usability:

In 251 cases out of 256, the results that the preparations according to this invention were improved from the viewpoint of simplicity and the sanitary aspect upon their use compared with the conventional vial preparations were obtained as replies collected from doctors in charge after the use. For example, according to the results of 105 replies which had been collected definitely, 100 replies (95%) recognized that the preparations of this invention were good in simplicity (other replies were due to the unskillfulness in operation of machinery). Besides, in the sanitary aspect, 101 replies (96%) out of 105 recognized that the preparations of this invention were improved in the sanitary aspect. According to the comments of the doctors in charge, the good simplicity and excellent sanitation upon the use of the preparation were recognized in the following respects. Namely, the syringe preparations according to this invention were recognized to have the following advantages. i) There was no potential problem of bacterial contamination and mixing of foreign matter. ii) Labors required in complicated operation of the transfer of the drug solution and the like were saved, whereby the operation time could be shortened. As a result, the injection time of a contrast medium was kept constant, and a test schedule became easy to make out. iii) The mistake of dosage, kind or the like, which occurred upon the preparation of a drug solution, could be avoided (the concentrations of the drug and preparation could be confirmed from a label on the syringe preparation), and waste matter (vials) became reduced. iv) The syringe preparations could be set in an automatic injector, and an imaging effect was obtained stably even by a fine needle. v) The syringe preparations were free from the loss of the drug solution due to its transfer.

From the above-described results, the syringe preparations of this invention were recognized to have a great many of excellent aspects in the usability as described above compared with the conventional vial preparations. The features of the syringe preparations according to this invention could hence be confirmed.

Example 11

A syringe preparation charged with a drug was obtained by injection-molding a portion of the resin prepared in Example 1 and charging an oily preparation having the following formulation into the resulting molding.

| Dimercaprol | 100 mg |
| Benzyl benzoate | 2 mg |
| arachis oil | To 1 ml |

Example 12

A syringe preparation charged with a drug was obtained by injection-molding a portion of the resin prepared in Example 1 and charging a fat emulsion having the following formulation into the resulting molding.

| Soybean oil | 100 mg |
| Yolk lecithin | 10 mg |
| Glycerol | 25 mg |
| Water for injection | To 1 ml |

INDUSTRIAL APPLICABILITY

According to the present invention, there are provided drug containing preparations, which are excellent in transparency, free from the dissolution of additives for a resin into a drug solution charged therein even when the drug solution remains charged for a long period of time and hence high in safety. These preparations are useful, in particular, as syringe preparations charged with a drug solution therein.

We claim:

1. A transparent syringe prefilled with a drug solution, said transparent syringe having been obtained by molding a resin composition comprising, as a base material, a propylene polymer, and as a nucleating agent, a phosphoric ester represented by the following general formula (1):

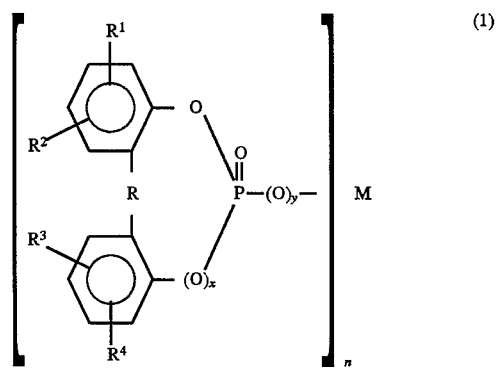

wherein $R^1$, $R^2$, $R^3$ and $R^4$ mean individually a hydrogen atom or a straight-chain, branched or cyclic alkyl which may be substituted, R denotes a direct bond, sulfur atom or alkylidene group, x and y stand individually for 0 or 1, M denotes a metal atom, and n means a valence of the metal, said transparent syringe, prefilled with a drug maintaining its transparency and being free Of contamination upon prolonged storage of at least 6 months at 40° C.

2. The transparent syringe as claimed in claim 1, wherein the drug solution is a contrast medium.

3. The transparent syringe as claimed in claim 1, wherein the drug solution is a solution comprising, as a principal ingredient, iohexol.

4. The transparent syringe as claimed in claim 1, wherein the propylene polymer is selected from the group consisting of (i) propylene homopolymers, (ii) crystalline copolymers with other monomers which are composed mainly of propylene, and (iii) blends of crystalline polypropylene as a principal component and other polymers, said homopolymers, copolymers and blends having a melt flow index of 0.5–100 g/10 min as measured in accordance with ASTM D-1238.

5. A transparent syringe body as claimed in claim 1, wherein said nucleating agent is methylene bis(2,4-di-tert-butylphenol)-phosphate.

6. The transparent syringe as claimed in claim 1, wherein said phosphoric ester represented by formula (1) is the sole nucleating agent.

7. The transparent syringe as claimed in claim 1, wherein said resin composition consists essentially of said base material and said nucleating agent.

8. The transparent syringe as claimed in claim 1, wherein said resin composition consists of said base material and said nucleating agent.

* * * * *

UNITED STATES PATENT AND TRADEMARK OFFICE
CERTIFICATE OF CORRECTION

PATENT NO. : 5,653,693
DATED : August 5, 1997
INVENTOR(S) : Akira MIWA, et al.

It is certified that error appears in the above-identified patent and that said Letters Patent is hereby corrected as shown below:

Column 24, line 58, "Of contamination" should read
--of contamination--.

Signed and Sealed this

Thirteenth Day of January, 1998

Attest:

BRUCE LEHMAN

*Attesting Officer*  *Commissioner of Patents and Trademarks*